United States Patent
Hart

(10) Patent No.: US 9,592,194 B2
(45) Date of Patent: *Mar. 14, 2017

(54) LIP STICK

(71) Applicant: Mary Kay Inc., Addison, TX (US)

(72) Inventor: Linda A. Hart, Dallas, TX (US)

(73) Assignee: Mary Kay Inc., Addison, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 14/693,381

(22) Filed: Apr. 22, 2015

(65) Prior Publication Data

US 2015/0224050 A1    Aug. 13, 2015

Related U.S. Application Data

(63) Continuation of application No. 13/471,026, filed on May 14, 2012, now Pat. No. 9,044,621.

(60) Provisional application No. 61/486,061, filed on May 13, 2011.

(51) Int. Cl.
| | |
|---|---|
| A61K 8/97 | (2006.01) |
| A61K 8/92 | (2006.01) |
| A61K 8/37 | (2006.01) |
| A61Q 1/06 | (2006.01) |
| A61K 8/29 | (2006.01) |
| A61K 8/67 | (2006.01) |
| A61Q 19/00 | (2006.01) |

(52) U.S. Cl.
CPC .............. *A61K 8/97* (2013.01); *A61K 8/29* (2013.01); *A61K 8/375* (2013.01); *A61K 8/678* (2013.01); *A61K 8/922* (2013.01); *A61Q 1/06* (2013.01); *A61Q 19/001* (2013.01); *A61K 2800/31* (2013.01); *A61K 2800/43* (2013.01)

(58) Field of Classification Search
None
See application file for complete search history.

(56) References Cited

U.S. PATENT DOCUMENTS

| | | | |
|---|---|---|---|
| 5,436,006 A | 7/1995 | Hirose et al. | 424/401 |
| 5,776,441 A | 7/1998 | Scancarella et al. | 424/61 |
| 6,555,097 B1 | 4/2003 | Rabe et al. | 424/64 |
| 6,582,748 B1 | 6/2003 | Loh et al. | 426/601 |
| 6,613,338 B1 | 9/2003 | Schreiber et al. | 424/401 |
| 7,001,603 B2 | 2/2006 | Bagdi et al. | 424/401 |
| 7,060,303 B2 | 6/2006 | Jones | 424/725 |
| 2007/0190186 A1 | 8/2007 | Loh et al. | 424/725 |
| 2007/0196301 A1 | 8/2007 | Blin et al. | 424/64 |
| 2008/0089916 A1 | 4/2008 | Magee et al. | 424/401 |
| 2008/0233064 A1 | 9/2008 | Tabakman et al. | 424/63 |
| 2008/0272668 A1 | 11/2008 | Baars et al. | 424/401 |
| 2009/0074685 A1 | 3/2009 | Lai | 424/59 |
| 2009/0324519 A1 | 12/2009 | Mori | 424/59 |
| 2012/0014887 A1* | 1/2012 | Fournial | A61K 8/64 424/59 |

FOREIGN PATENT DOCUMENTS

| | | |
|---|---|---|
| FR | 2806273 A | 9/2001 |
| WO | WO 2010/082175 | 7/2010 |
| WO | WO 2010/082176 | 7/2010 |
| WO | WO 2010/082177 | 7/2010 |

OTHER PUBLICATIONS

PCT International Search Report and Written Opinion issued in PCT Application No. PCT/US2012/037805, dated Nov. 30, 2012.
Final Report—2004. Int J Toxicol. 2004;23 Suppl 2:55-94. [no authors listed] Final report of the amended safety assessment of Glyceryl Laurate, Glyceryl Laurate SE, Glyceryl Laurate/Oleate, Glyceryl Adipate, Glyceryl Alginate, Glyceryl Arachidate, Glyceryl Arachidonate, Glyceryl Behenate, Glyceryl Caprate, Glyceryl Caprylate, Glyceryl . . . .
FDA GRAS list—2014. [Downloaded on Oct. 27, 2014 from the website http://www.accessdata. fda.gov/scripts/cdrh/cfdocs/cfcfr/CFRSearch .cfm?fr= 1 84.1328].
GoodGuide—2014. Downloaded on Oct. 27, 2014 from the website http://www.goodguide.com/ingredients/383926-glycerylbehenate-eicosanoate-ingredient-information-reviews].

* cited by examiner

*Primary Examiner* — Sue Liu
*Assistant Examiner* — Thor Nielsen
(74) *Attorney, Agent, or Firm* — Norton Rose Fulbright US LLP

(57) ABSTRACT

Disclosed is a lipstick comprising a combination of active ingredients comprising *Portulaca pilosa* extract, sunflower oil, jojoba esters, mango butter, and tocopherol.

9 Claims, No Drawings

LIP STICK

CROSS REFERENCE TO RELATED APPLICATIONS

This application is continuation of U.S. patent application Ser. No. 13/471,026, filed May 14, 2012, which claims the benefit of U.S. Provisional Application No. 61/486,061, filed May 13, 2011. The contents of the referenced applications are incorporated herein by reference.

BACKGROUND OF THE INVENTION

A. Field of the Invention

The present invention relates generally to lip-based compositions such as lipsticks. In particular, the present invention concerns a lip-based composition that has the ability to color lips, protect the lips from moisture loss and free-radical damage, and also increase collagen and hyaluronic acid production in the lips. This can advantageously result in lips that have a fuller appearance while reducing the appearance of fine lines present on lips.

B. Description of Related Art

Previous attempts at lip-based products such as lip sticks have either lacked substantivity, tended to dry-out and clump or crack on the lip, or lacked the ability to effectively treat or prevent lip-related conditions (e.g., dried or cracked lips, lip wrinkles, etc.). Attempts to solve these problems have led to formulations that were difficult to spread on the lips, had unpleasant tactile properties (e.g., heavy, oily, tacky, etc.), and had limited beneficial effects for lip-related conditions. This resulted in lips that had an unpleasant aesthetic appearance and a streaky/non-uniform coloring.

SUMMARY OF THE INVENTION

The inventor found a solution to the aforementioned problems. This solution results in a lip-based product such as lipstick that is substantive, does not pool on the lips, is easy to spread, and has effective amounts of actives to moisturize the lips, treat dry, chapped, or cracked lips, and reduce or prevent the appearance of lip wrinkles. The lip-based product also has pleasant tactile properties and provides aesthetically pleasing visual appearance on the lips. This is achieved by a unique combination of the following ingredients: a combination of active ingredients comprising *Portulaca pilosa* extract, sunflower oil, jojoba esters, mango butter, and tocopherol; and a dermatologically acceptable carrier comprising glyceryl behenate/eicosadioate. In particular aspects, the composition can also include peptides that can further enhance the efficacy of the lip-based composition. Also, the *Portulaca pilosa* extract can be an oil-based extract. The lipstick can include water or can be anhydrous. The lipstick can be in a semi-solid or in a solid form. The lipstick can have a drop point of 53-55° C. and a melt point of 49-51° C. In particular instances, the dermatologically acceptable carrier further comprises orange peel wax, *Limnanthes alba* seed oil, *Butyrospermum parkii*, ethyl macadamiate, sucrose acetate isobutyrate, sunflower wax, candelilla wax, beeswax, titanium dioxide, mica silk, or castor oil, or any combination thereof, or all of these ingredients. The lipstick can further include colorants or dyes so as to obtain a desired color or shade. In certain aspects, the lipstick includes 10 to 15% by weight of the lipstick of sunflower oil, 10 to 15% by weight of the lipstick of jojoba esters, 3 to 7% by weight of the lipstick of mango butter, 0.1 to 1% by weight of the lipstick of tocopherol, and 0.1 to 1% by weight of the lipstick of glyceryl behenate/eicosadioate. The lipstick can further include 1 to 3% by weight of the lipstick of orange peel wax, 3 to 7% by weight of the lipstick of a mixture of *Limnanthes alba* seed oil and *Butyrospermum parkii*, 3 to 7% by weight of the lipstick of ethyl macadamiate, 2 to 5% by weight of the lipstick of sucrose acetate isobutyrate, 2 to 5% by weight of the lipstick of sunflower wax, 3 to 7% by weight of the lipstick of candelilla wax, 2 to 5% by weight of the lipstick of beeswax, 5 to 10% by weight of the lipstick of titanium dioxide, 2 to 5% by weight of the lipstick of mica silk, and 13 to 17% by weight of the lipstick of castor oil. In some instances, the lipstick excludes the following ingredients: a fatty acid; a polyamide; and/or a polyglyceryl-10 behenate/eicosanedioate. The lipstick can be formed into an elongated shape or stick and can be inside a container that has a base and a cap (e.g., a lipstick container).

In one particular instance there is disclosed an anhydrous lipstick that includes 11 to 13% by weight of sunflower oil, 12 to 14% by weight of jojoba esters, 4 to 6% by weight of mango butter, 0.1 to 1% by weight of tocopherol, 0.1 to 1% by weight of glyceryl behenate/eicosadioate, 1 to 3% by weight of orange peel wax, 4 to 6% by weight of a mixture of *Limnanthes alba* seed oil and *Butyrospermum parkii*, 5 to 7% by weight of ethyl macadamiate, 2 to 3% by weight of sucrose acetate isobutyrate, 2 to 4% by weight of sunflower wax, 4 to 6% by weight of candelilla wax, 2 to 4% by weight of beeswax, 7 to 10% by weight of titanium dioxide, 2 to 4% by weight of mica silk, and 13 to 17% by weight of castor oil. The lipstick can be anhydrous or can include water. The lipstick can further comprise a peptide to enhance the efficacy of the lipstick. The lipstick can have a drop point of 53-55° C. and a melt point of 49-51° C.

The lipstick of the present invention can be applied at least once, twice, three, four, or more times a day. Once applied, the lipsticks can remain on the skin for at least 10, 20, 30, or 60 minutes, 1, 2, 3, 4, 5, 6, 7, 8, 9, 10, 11, or 12 hours, or longer. The lipsticks can also include any one of or any combination of cosmetic and/or pharmaceutical ingredients disclosed in this specification. For instance, lipsticks can include ingredients from at least one, two, three, four, five, six, and/or seven of the following categories: (1) moisturizing agents; (2) antioxidants; (3) structuring agents; (4) silicone containing compounds; (5) essential oils (6) thickening agents; and/or (7) preservatives.

It is also contemplated that the viscosity of the lip stick compositions can be selected to achieve a desired result (e.g., depending on the type of composition desired, the viscosity of such composition can be from about 1 cps to well over 1 million cps or any range or integer derivable therein (e.g., 2 cps, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, 200000, 300000, 400000, 500000, 600000, 700000, 800000, 900000, 1000000, cps, etc., as measured on a Brookfield Viscometer using a TC spindle at 2.5 rpm at 25° C.). The compositions in non-limiting aspects can have a pH of about 6 to about 9. In other aspects, the pH can be 1, 2, 3, 4, 5, 6, 7, 8, 9, 10, 11, 12, 13, or 14. In other aspects, the compositions can be sunscreens having a sun protection factor (SPF) of 1, 5, 10, 15, 20, 25, 30, 35, 40, 45, 50, 55, or more.

The lipsticks can have a cosmetically or pharmaceutically elegant feel such a non-oily, non-greasy, non-sticky, non-tacky, and/or silky feel after being applied to skin such as hand skin.

Also disclosed is a method for moisturizing lips, treating dried, cracked, or chapped lips or skin in the vermillion border or preventing or reducing the appearance of lip wrinkles or wrinkles in the vermillion border, or erythemic (i.e., red or inflamed skin) in the vermillion border, comprising topically applying any one of the lipsticks disclosed in this application or any one of the mixtures disclosed in this application to dried, cracked, or chapped lips or to skin in need of prevention or reduction of lip wrinkles, wherein topical application of the compositions or mixtures moisturizes the lips, treats dried, cracked, or chapped lips or prevents or reduces the appearance of lip wrinkles. The composition can be applied directly onto the lips or can be applied onto lips that already have lipstick or lip balm applied thereon. The lip-based compositions can also be used to increase the production of collagen and hyaluronic acid in the lips via topical application of the composition to lips in need of increased collagen production and hyaluronic acid production.

"Vermillion border" means the normally sharp demarcation between the lip (red colored) and the adjacent normal skin. It represents the change in the epidermis from highly keratinized external skin to less keratinized internal skin. It has no sebaceous glands, sweat glands, or hair.

"Topical application" means to apply or spread a composition onto the surface of lips or keratinous tissue. "Topical skin composition" includes compositions suitable for topical application on lips or keratinous tissue. Such compositions are typically dermatologically-acceptable in that they do not have undue toxicity, incompatibility, instability, allergic response, and the like, when applied to lips or skin. Topical skin care compositions of the present invention can have a selected viscosity to avoid significant dripping or pooling after application to skin.

"Keratinous tissue" includes keratin-containing layers disposed as the outermost protective covering of mammals and includes, but is not limited to, lips, skin, hair and nails.

The term "about" or "approximately" are defined as being close to as understood by one of ordinary skill in the art, and in one non-limiting embodiment the terms are defined to be within 10%, preferably within 5%, more preferably within 1%, and most preferably within 0.5%.

The term "substantially" and its variations are defined as being largely but not necessarily wholly what is specified as understood by one of ordinary skill in the art, and in one non-limiting embodiment substantially refers to ranges within 10%, within 5%, within 1%, or within 0.5%.

The terms "inhibiting" or "reducing" or any variation of these terms, when used in the claims and/or the specification includes any measurable decrease or complete inhibition to achieve a desired result.

The term "effective," as that term is used in the specification and/or claims, means adequate to accomplish a desired, expected, or intended result.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The lipsticks, compositions, and methods for their use can "comprise," "consist essentially of," or "consist of" any of the ingredients or steps disclosed throughout the specification. With respect to the transitional phase "consisting essentially of," in one non-limiting aspect, a basic and novel characteristic of the lipsticks and methods disclosed in this specification includes the lipstick's ability to moisturize lips while remaining on the lips for a prolonged period of time (for at least 1 hour).

Other objects, features and advantages of the present invention will become apparent from the following detailed description. It should be understood, however, that the detailed description and the examples, while indicating specific embodiments of the invention, are given by way of illustration only. Additionally, it is contemplated that changes and modifications within the spirit and scope of the invention will become apparent to those skilled in the art from this detailed description.

DESCRIPTION OF ILLUSTRATIVE EMBODIMENTS

A. Lip-Based Formulations

One of the unique aspects of the present invention is a lip-based formulation such as an anhydrous lipstick that has a pleasant tactile property along with effective moisturizing and anti-aging capabilities. The effectiveness of the composition resides in the synergistic combination of sunflower oil, jojoba esters, mango butter, tocopherol, and *Portulaca pilosa* extract. The International Cosmetic Ingredient Dictionary and Handbook, $12^{th}$ Edition (2008) provides descriptions of these ingredients and commercial sources of their availability. For the *Portulaca pilosa* extract, this ingredient is from the *Portulaca pilosa* plant, which is a species of flowering plant in the purslane family, Portulacaceae. This plant is native to the United States. It is a succulent with linear green leaves and is capable of producing pink flowers. Oil-based extracts from *Portulaca pilosa* can be obtained by using either the whole plant or part of the plant (e.g., leaves, roots, flowers, etc.). In particular embodiments, the whole plant is used. For instance the plant (or any part of the plant) can be mascerated and subjected to an oil-based solution to obtain the extract. The extract can then filtered and packaged for storage or be added to a composition of the present invention. Alternatively, the extract can be purchased from a commercial source (e.g., a product having such an extract is available from Sederma (France) under the trade name Volulip™, which is used in the exemplary formulations in the Examples section of this specification). Volulip™ also includes a tri-peptide (palmitoyl-$KMO_2K$), cetearyl Ethylhexanoate, sorbitan isostearate, and sucrose cocoate.

As shown in the examples, an acceptable dermatologically acceptable vehicle for the actives can include glyceryl behenate/eicosadioate, which is a mixture of esters of glycerin with behenic and eicosandioic acids. It too is commercially available from a wide range of sources (see International Cosmetic Ingredient Dictionary and Handbook, $12^{th}$ Edition (2008), Volume 1, page 1065). It was discovered that this ingredient structures the lipstick of the present invention in a manner that increases stability while providing for an aesthetically pleasing tactile property. The dermatologically acceptable vehicle can also include orange peel wax, *Limnanthes alba* seed oil, *Butyrospermum parkii*, ethyl macadamiate, sucrose acetate isobutyrate, sunflower wax, candelilla wax, beeswax, titanium dioxide, mica silk, and castor oil, all of which provide additional structuring benefits for the lipstick of the present invention.

Example 1, Table 3, in the Examples section provides a non-limiting way to make a lipstick having the characteristics described throughout this specification.

While particular embodiments and amounts are described throughout this specification, it is contemplated that the compositions of the present invention can include these ingredients along with any number of combinations of additional ingredients described throughout this specification. The concentrations of any ingredient within the compositions can vary. In non-limiting embodiments, for example, the compositions can comprise, consisting essentially of, or consist of, in their final form, for example, at least about 0.0001%, 0.0002%, 0.0003%, 0.0004%, 0.0005%, 0.0006%, 0.0007%, 0.0008%, 0.0009%, 0.0010%, 0.0011%, 0.0012%, 0.0013%, 0.0014%, 0.0015%, 0.0016%, 0.0017%, 0.0018%, 0.0019%, 0.0020%, 0.0021%, 0.0022%, 0.0023%, 0.0024%, 0.0025%, 0.0026%, 0.0027%, 0.0028%, 0.0029%, 0.0030%, 0.0031%, 0.0032%, 0.0033%, 0.0034%, 0.0035%, 0.0036%, 0.0037%, 0.0038%, 0.0039%, 0.0040%, 0.0041%, 0.0042%, 0.0043%, 0.0044%, 0.0045%, 0.0046%, 0.0047%, 0.0048%, 0.0049%, 0.0050%, 0.0051%, 0.0052%, 0.0053%, 0.0054%, 0.0055%, 0.0056%, 0.0057%, 0.0058%, 0.0059%, 0.0060%, 0.0061%, 0.0062%, 0.0063%, 0.0064%, 0.0065%, 0.0066%, 0.0067%, 0.0068%, 0.0069%, 0.0070%, 0.0071%, 0.0072%, 0.0073%, 0.0074%, 0.0075%, 0.0076%, 0.0077%, 0.0078%, 0.0079%, 0.0080%, 0.0081%, 0.0082%, 0.0083%, 0.0084%, 0.0085%, 0.0086%, 0.0087%, 0.0088%, 0.0089%, 0.0090%, 0.0091%, 0.0092%, 0.0093%, 0.0094%, 0.0095%, 0.0096%, 0.0097%, 0.0098%, 0.0099%, 0.0100%, 0.0200%, 0.0250%, 0.0275%, 0.0300%, 0.0325%, 0.0350%, 0.0375%, 0.0400%, 0.0425%, 0.0450%, 0.0475%, 0.0500%, 0.0525%, 0.0550%, 0.0575%, 0.0600%, 0.0625%, 0.0650%, 0.0675%, 0.0700%, 0.0725%, 0.0750%, 0.0775%, 0.0800%, 0.0825%, 0.0850%, 0.0875%, 0.0900%, 0.0925%, 0.0950%, 0.0975%, 0.1000%, 0.1250%, 0.1500%, 0.1750%, 0.2000%, 0.2250%, 0.2500%, 0.2750%, 0.3000%, 0.3250%, 0.3500%, 0.3750%, 0.4000%, 0.4250%, 0.4500%, 0.4750%, 0.5000%, 0.5250%, 0.0550%, 0.5750%, 0.6000%, 0.6250%, 0.6500%, 0.6750%, 0.7000%, 0.7250%, 0.7500%, 0.7750%, 0.8000%, 0.8250%, 0.8500%, 0.8750%, 0.9000%, 0.9250%, 0.9500%, 0.9750%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, 6.0%, 6.1%, 6.2%, 6.3%, 6.4%, 6.5%, 6.6%, 6.7%, 6.8%, 6.9%, 7.0%, 7.1%, 7.2%, 7.3%, 7.4%, 7.5%, 7.6%, 7.7%, 7.8%, 7.9%, 8.0%, 8.1%, 8.2%, 8.3%, 8.4%, 8.5%, 8.6%, 8.7%, 8.8%, 8.9%, 9.0%, 9.1%, 9.2%, 9.3%, 9.4%, 9.5%, 9.6%, 9.7%, 9.8%, 9.9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 60%, 65%, 70%, 75%, 80%, 85%, 90%, 95%, or 99% or any range derivable therein. In non-limiting aspects, the percentage can be calculated by weight or volume of the total composition. A person of ordinary skill in the art would understand that the concentrations can vary depending on the addition, substitution, and/or subtraction of ingredients in a given composition.

The disclosed compositions of the present invention may also include various antioxidants to retard oxidation of one or more components. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

In addition to lipsticks and lip glosses of the present invention, the combination of active ingredients can be used in other cosmetically and dermalogically acceptable formulations. Non-limiting examples of suitable vehicles include creams, lotions, and ointments. Variations and other appropriate vehicles will be apparent to the skilled artisan and are appropriate for use in the present invention. In certain aspects, it is important that the concentrations and combinations of the compounds, ingredients, and agents be selected in such a way that the combinations are chemically compatible and do not form complexes which precipitate from the finished product. Such additional formulations can, for example, moisturize skin, increase collagen production in skin, increase hyaluronic acid production in skin, reduce the appearance of fine lines and wrinkles, and firm-up skin such as loose or sagging skin.

B. Additional Ingredients

The lipsticks, lip glosses, and compositions of the present invention can also include additional ingredients such as cosmetic ingredients and pharmaceutical active ingredients. Non-limiting examples of these additional ingredients are described in the following subsections.

1. Cosmetic Ingredients

The CTFA International Cosmetic Ingredient Dictionary and Handbook (2004 and 2008) describes a wide variety of non-limiting cosmetic ingredients that can be used in the context of the present invention. Examples of these ingredient classes include: fragrances (artificial and natural), dyes and color ingredients (e.g., Blue 1, Blue 1 Lake, Red 40, titanium dioxide, D&C blue no. 4, D&C green no. 5, D&C orange no. 4, D&C red no. 17, D&C red no. 33, D&C violet no. 2, D&C yellow no. 10, and D&C yellow no. 11), adsorbents, lubricants, solvents, moisturizers (including, e.g., emollients, humectants, film formers, occlusive agents, and agents that affect the natural moisturization mechanisms of the skin), water-repellants, UV absorbers (physical and chemical absorbers such as paraaminobenzoic acid ("PABA") and corresponding PABA derivatives, titanium dioxide, zinc oxide, etc.), essential oils, vitamins (e.g. A, B, C, D, E, and K), trace metals (e.g. zinc, calcium and selenium), anti-irritants (e.g. steroids and non-steroidal anti-inflammatories), botanical extracts (e.g. *aloe vera*, chamomile, cucumber extract, *ginkgo biloba, ginseng*, and rosemary), anti-microbial agents, antioxidants (e.g., BHT and tocopherol), chelating agents (e.g., disodium EDTA and tetrasodium EDTA), preservatives (e.g., methylparaben and propylparaben), pH adjusters (e.g., sodium hydroxide and citric acid), absorbents (e.g., aluminum starch octenylsuccinate, kaolin, corn starch, oat starch, cyclodextrin, talc, and zeolite), skin bleaching and lightening agents (e.g., hydroquinone and niacinamide lactate), humectants (e.g., sorbitol, urea, and manitol), exfoliants, waterproofing agents (e.g., magnesium/aluminum hydroxide stearate), skin conditioning agents (e.g., *aloe* extracts, allantoin, bisabolol, ceramides, dimethicone, hyaluronic acid, and dipotassium glycyrrhizate). Non-limiting examples of some of these ingredients are provided in the following subsections.

a. Moisturizing Agents

Non-limiting examples of moisturizing agents that can be used with the compositions of the present invention include amino acids, chondroitin sulfate, diglycerin, erythritol, fructose, glucose, glycerin, glycerol polymers, glycol, 1,2,6-hexanetriol, honey, hyaluronic acid, hydrogenated honey, hydrogenated starch hydrolysate, inositol, lactitol, maltitol, maltose, mannitol, natural moisturizing factor, PEG-15 butanediol, polyglyceryl sorbitol, salts of pyrollidone carboxylic acid, potassium PCA, propylene glycol, sodium glucuronate, sodium PCA, sorbitol, sucrose, trehalose, urea, and xylitol.

Other examples include acetylated lanolin, acetylated lanolin alcohol, alanine, algae extract, *aloe barbadensis*, *aloe-barbadensis* extract, *aloe barbadensis* gel, *althea officinalis* extract, apricot (*prunus armeniaca*) kernel oil, arginine, arginine aspartate, *arnica montana* extract, aspartic acid, avocado (*persea gratissima*) oil, barrier sphingolipids, butyl alcohol, beeswax, behenyl alcohol, beta-sitosterol, birch (*betula alba*) bark extract, borage (*borago officinalis*) extract, butcherbroom (*ruscus aculeatus*) extract, butylene glycol, *calendula officinalis* extract, *calendula officinalis* oil, candelilla (*euphorbia cerifera*) wax, canola oil, caprylic/capric triglyceride, cardamon (*elettaria cardamomum*) oil, carnauba (*copernicia cerifera*) wax, carrot (*daucus carota sativa*) oil, castor (*ricinus communis*) oil, ceramides, ceresin, ceteareth-5, ceteareth-12, ceteareth-20, cetearyl octanoate, ceteth-20, ceteth-24, cetyl acetate, cetyl octanoate, cetyl palmitate, chamomile (*anthemis nobilis*) oil, cholesterol, cholesterol esters, cholesteryl hydroxystearate, citric acid, clary (*salvia sclarea*) oil, cocoa (*theobroma cacao*) butter, coco-caprylate/caprate, coconut (*cocos nucifera*) oil, collagen, collagen amino acids, corn (*zea mays*) oil, fatty acids, decyl oleate, dimethicone copolyol, dimethiconol, dioctyl adipate, dioctyl succinate, dipentaerythrityl hexacaprylate/hexacaprate, DNA, erythritol, ethoxydiglycol, ethyl linoleate, *eucalyptus globulus* oil, evening primrose (*oenothera biennis*) oil, fatty acids, *geranium maculatum* oil, glucosamine, glucose glutamate, glutamic acid, glycereth-26, glycerin, glycerol, glyceryl distearate, glyceryl hydroxystearate, glyceryl laurate, glyceryl linoleate, glyceryl myristate, glyceryl oleate, glyceryl stearate, glyceryl stearate SE, glycine, glycol stearate, glycol stearate SE, glycosaminoglycans, grape (*vitis vinifera*) seed oil, hazel (*corylus americana*) nut oil, hazel (*corylus avellana*) nut oil, hexylene glycol, hyaluronic acid, hybrid safflower (*carthamus tinctorius*) oil, hydrogenated castor oil, hydrogenated coco-glycerides, hydrogenated coconut oil, hydrogenated lanolin, hydrogenated lecithin, hydrogenated palm glyceride, hydrogenated palm kernel oil, hydrogenated soybean oil, hydrogenated tallow glyceride, hydrogenated vegetable oil, hydrolyzed collagen, hydrolyzed elastin, hydrolyzed glycosaminoglycans, hydrolyzed keratin, hydrolyzed soy protein, hydroxylated lanolin, hydroxyproline, isocetyl stearate, isocetyl stearoyl stearate, isodecyl oleate, isopropyl isostearate, isopropyl lanolate, isopropyl myristate, isopropyl palmitate, isopropyl stearate, isostearamide DEA, isostearic acid, isostearyl lactate, isostearyl neopentanoate, jasmine (*jasminum officinale*) oil, jojoba (*buxus chinensis*) oil, kelp, kukui (*aleurites moluccana*) nut oil, lactamide MEA, laneth-16, laneth-10 acetate, lanolin, lanolin acid, lanolin alcohol, lanolin oil, lanolin wax, lavender (*lavandula angustifolia*) oil, lecithin, lemon (*citrus medica limonum*) oil, linoleic acid, linolenic acid, *macadamia ternifolia* nut oil, maltitol, *matricaria* (*chamomilla recutita*) oil, methyl glucose sesquistearate, methylsilanol PCA, mineral oil, mink oil, mortierella oil, myristyl lactate, myristyl myristate, myristyl propionate, neopentyl glycol dicaprylate/dicaprate, octyldodecanol, octyldodecyl myristate, octyldodecyl stearoyl stearate, octyl hydroxystearate, octyl palmitate, octyl salicylate, octyl stearate, oleic acid, olive (*olea europaea*) oil, orange (*citrus aurantium dulcis*) oil, palm (*elaeis guineensis*) oil, palmitic acid, pantethine, panthenol, panthenyl ethyl ether, paraffin, PCA, peach (*prunus persica*) kernel oil, peanut (*arachis hypogaea*) oil, PEG-8 C12-18 ester, PEG-15 cocamine, PEG-150 distearate, PEG-60 glyceryl isostearate, PEG-5 glyceryl stearate, PEG-30 glyceryl stearate, PEG-7 hydrogenated castor oil, PEG-40 hydrogenated castor oil, PEG-60 hydrogenated castor oil, PEG-20 methyl glucose sesquistearate, PEG40 sorbitan peroleate, PEG-5 soy sterol, PEG-10 soy sterol, PEG-2 stearate, PEG-8 stearate, PEG-20 stearate, PEG-32 stearate, PEG-40 stearate, PEG-50 stearate, PEG-100 stearate, PEG-150 stearate, pentadecalactone, peppermint (*mentha piperita*) oil, petrolatum, phospholipids, polyamino sugar condensate, polyglyceryl-3 diisostearate, polyquaternium-24, polysorbate 20, polysorbate 40, polysorbate 60, polysorbate 80, polysorbate 85, potassium myristate, potassium palmitate, propylene glycol, propylene glycol dicaprylate/dicaprate, propylene glycol dioctanoate, propylene glycol dipelargonate, propylene glycol laurate, propylene glycol stearate, propylene glycol stearate SE, PVP, pyridoxine dipalmitate, retinol, retinol palmitate, rice (*oryza sativa*) bran oil, RNA, rosemary (*rosmarinus officinalis*) oil, rose oil, safflower (*carthamus tinctorius*) oil, sage (*salvia officinalis*) oil, sandalwood (*santalum album*) oil, serine, serum protein, sesame (*sesamum indicum*) oil, shea butter (*butyrospermum parkii*), silk powder, sodium chondroitin sulfate, sodium hyaluronate, sodium lactate, sodium palmitate, sodium PCA, sodium polyglutamate, soluble collagen, sorbitan laurate, sorbitan oleate, sorbitan palmitate, sorbitan sesquioleate, sorbitan stearate, sorbitol, soybean (*glycine soja*) oil, sphingolipids, squalane, squalene, stearamide MEA-stearate, stearic acid, stearoxy dimethicone, stearoxytrimethylsilane, stearyl alcohol, stearyl glycyrrhetinate, stearyl heptanoate, stearyl stearate, sunflower (*helianthus annuus*) seed oil, sweet almond (*prunus amygdalus dulcis*) oil, synthetic beeswax, tocopherol, tocopheryl acetate, tocopheryl linoleate, tribehenin, tridecyl neopentanoate, tridecyl stearate, triethanolamine, tristearin, urea, vegetable oil, water, waxes, wheat (*triticum vulgare*) germ oil, and ylang ylang (*cananga odorata*) oil.

b. Antioxidants

Non-limiting examples of antioxidants that can be used with the compositions of the present invention include acetyl cysteine, ascorbic acid polypeptide, ascorbyl dipalmitate, ascorbyl methylsilanol pectinate, ascorbyl palmitate, ascorbyl stearate, BHA, BHT, t-butyl hydroquinone, cysteine, cysteine HCl, diamylhydroquinone, di-t-butylhydroquinone, dicetyl thiodipropionate, dioleyl tocopheryl methylsilanol, disodium ascorbyl sulfate, distearyl thiodipropionate, ditridecyl thiodipropionate, dodecyl gallate, erythorbic acid, esters of ascorbic acid, ethyl ferulate, ferulic acid, gallic acid esters, hydroquinone, isooctyl thioglycolate, kojic acid, magnesium ascorbate, magnesium ascorbyl phosphate, methylsilanol ascorbate, natural botanical anti-oxidants such as green tea or grape seed extracts, nordihydroguaiaretic acid, octyl gallate, phenylthioglycolic acid, potassium ascorbyl tocopheryl phosphate, potassium sulfite, propyl gallate, quinones, rosmarinic acid, sodium ascorbate, sodium bisulfite, sodium erythorbate, sodium metabisulfite, sodium sulfite, superoxide dismutase, sodium thioglycolate, sorbityl furfural, thiodiglycol, thiodiglycolamide, thiodiglycolic acid, thioglycolic acid, thiolactic acid, thiosalicylic acid, tocophereth-5, tocophereth-10, tocophereth-12, tocophereth-18, tocophereth-50, tocopherol, tocophersolan, tocopheryl acetate, tocopheryl linoleate, tocopheryl nicotinate, tocopheryl succinate, and tris(nonylphenyl)phosphite.

c. Structuring Agents

In other non-limiting aspects, the compositions of the present invention can include a structuring agent. Structuring agent, in certain aspects, assist in providing rheological characteristics to the composition to contribute to the composition's stability. In other aspects, structuring agents can also function as an emulsifier or surfactant. Non-limiting examples of structuring agents include stearic acid, palmitic acid, stearyl alcohol, cetyl alcohol, behenyl alcohol, stearic acid, palmitic acid, the polyethylene glycol ether of stearyl alcohol having an average of about 1 to about 21 ethylene oxide units, the polyethylene glycol ether of cetyl alcohol having an average of about 1 to about 5 ethylene oxide units, and mixtures thereof.

d. Silicone Containing Compounds

In non-limiting aspects, silicone containing compounds include any member of a family of polymeric products whose molecular backbone is made up of alternating silicon and oxygen atoms with side groups attached to the silicon atoms. By varying the —Si—O— chain lengths, side groups, and crosslinking, silicones can be synthesized into a wide variety of materials. They can vary in consistency from liquid to gel to solids.

The silicone containing compounds that can be used in the context of the present invention include those described in this specification or those known to a person of ordinary skill in the art. Non-limiting examples include silicone oils (e.g., volatile and non-volatile oils), gels, and solids. In certain aspects, the silicon containing compounds includes a silicone oils such as a polyorganosiloxane. Non-limiting examples of polyorganosiloxanes include dimethicone, cyclomethicone, polysilicone-11, phenyl trimethicone, trimethylsilylamodimethicone, stearoxytrimethylsilane, or mixtures of these and other organosiloxane materials in any given ratio in order to achieve the desired consistency and application characteristics depending upon the intended application (e.g., to a particular area such as the skin, hair, or eyes). A "volatile silicone oil" includes a silicone oil have a low heat of vaporization, i.e. normally less than about 50 cal per gram of silicone oil. Non-limiting examples of volatile silicone oils include: cyclomethicones such as Dow Corning 344 Fluid, Dow Corning 345 Fluid, Dow Corning 244 Fluid, and Dow Corning 245 Fluid, Volatile Silicon 7207 (Union Carbide Corp., Danbury, Conn.); low viscosity dimethicones, i.e. dimethicones having a viscosity of about 50 cst or less (e.g., dimethicones such as Dow Corning 200-0.5 cst Fluid). The Dow Corning Fluids are available from Dow Corning Corporation, Midland, Mich. Cyclomethicone and dimethicone are described in the Third Edition of the CTFA Cosmetic Ingredient Dictionary (incorporated by reference) as cyclic dimethyl polysiloxane compounds and a mixture of fully methylated linear siloxane polymers end-blocked with trimethylsiloxy units, respectively. Other non-limiting volatile silicone oils that can be used in the context of the present invention include those available from General Electric Co., Silicone Products Div., Waterford, N.Y. and SWS Silicones Div. of Stauffer Chemical Co., Adrian, Mich.

e. Essential Oils

Essential oils include oils derived from herbs, flowers, trees, and other plants. Such oils are typically present as tiny droplets between the plant's cells, and can be extracted by several method known to those of skill in the art (e.g., steam distilled, enfleurage (i.e., extraction by using fat), maceration, solvent extraction, or mechanical pressing). When these types of oils are exposed to air they tend to evaporate (i.e., a volatile oil). As a result, many essential oils are colorless, but with age they can oxidize and become darker. Essential oils are insoluble in water and are soluble in alcohol, ether, fixed oils (vegetal), and other organic solvents. Typical physical characteristics found in essential oils include boiling points that vary from about 160° to 240° C. and densities ranging from about 0.759 to about 1.096.

Essential oils typically are named by the plant from which the oil is found. For example, rose oil or peppermint oil are derived from rose or peppermint plants, respectively. Non-limiting examples of essential oils that can be used in the context of the present invention include sesame oil, *macadamia* nut oil, tea tree oil, evening primrose oil, Spanish sage oil, Spanish rosemary oil, coriander oil, thyme oil, pimento berries oil, rose oil, anise oil, balsam oil, bergamot oil, rosewood oil, cedar oil, chamomile oil, sage oil, clary sage oil, clove oil, cypress oil, *eucalyptus* oil, fennel oil, sea fennel oil, frankincense oil, *geranium* oil, ginger oil, grapefruit oil, jasmine oil, juniper oil, lavender oil, lemon oil, lemongrass oil, lime oil, mandarin oil, marjoram oil, myrrh oil, neroli oil, orange oil, patchouli oil, pepper oil, black pepper oil, petitgrain oil, pine oil, rose otto oil, rosemary oil, sandalwood oil, spearmint oil, spikenard oil, vetiver oil, wintergreen oil, or ylang ylang. Other essential oils known to those of skill in the art are also contemplated as being useful within the context of the present invention.

f. Thickening Agents

Thickening agents, including thickener or gelling agents, include substances which that can increase the viscosity of a composition. Thickeners includes those that can increase the viscosity of a composition without substantially modifying the efficacy of the active ingredient within the composition. Thickeners can also increase the stability of the compositions of the present invention. In certain aspects of the present invention, thickeners include hydrogenated polyisobutene or trihydroxystearin, or a mixture of both.

Non-limiting examples of additional thickening agents that can be used in the context of the present invention include carboxylic acid polymers, crosslinked polyacrylate polymers, polyacrylamide polymers, polysaccharides, and gums. Examples of carboxylic acid polymers include crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol (see U.S. Pat. Nos. 5,087,445; 4,509,949; 2,798,053; CTFA International Cosmetic Ingredient Dictionary, Fourth edition, 1991, pp. 12 and 80). Examples of commercially available carboxylic acid polymers include carbomers, which are homopolymers of acrylic acid crosslinked with allyl ethers of sucrose or pentaerytritol (e.g., Carbopol™ 900 series from B. F. Goodrich).

Non-limiting examples of crosslinked polyacrylate polymers include cationic and nonionic polymers. Examples are described in U.S. Pat. Nos. 5,100,660; 4,849,484; 4,835,206; 4,628,078; 4,599,379).

Non-limiting examples of polyacrylamide polymers (including nonionic polyacrylamide polymers including substituted branched or unbranched polymers) include polyacrylamide, isoparaffin and laureth-7, multi-block copolymers of acrylamides and substituted acrylamides with acrylic acids and substituted acrylic acids.

Non-limiting examples of polysaccharides include cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Another example is an alkyl substituted cellulose where the hydroxy groups of the cellulose polymer is hydroxyalkylated (preferably hydroxy ethylated or hydroxypropylated) to form a hydroxyalkylated cellulose which is then further modified with a $C_{10}$-$C_{30}$ straight chain or branched chain alkyl group through an ether linkage. Typically these polymers are ethers of $C_{10}$-$C_{30}$ straight or branched chain alcohols with hydroxyalkylcelluloses. Other useful polysaccharides include scleroglucans comprising a linear chain of (1-3) linked glucose units with a (1-6) linked glucose every three unit.

Non-limiting examples of gums that can be used with the present invention include *acacia*, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluroinic acid, hydrated silica, hydroxypropyl chitosan, hydroxypropyl guar, karaya gum, kelp, locust bean gum, natto gum, potassium alginate, potassium carrageenan, propylene glycol alginate, sclerotium gum, sodium carboyxmethyl dextran, sodium carrageenan, tragacanth gum, xanthan gum, and mixtures thereof.

g. Preservatives

Non-limiting examples of preservatives that can be used in the context of the present invention include quaternary ammonium preservatives such as polyquaternium-1 and benzalkonium halides (e.g., benzalkonium chloride ("BAC") and benzalkonium bromide), parabens (e.g., methylparabens and propylparabens), phenoxyethanol, benzyl alcohol, chlorobutanol, phenol, sorbic acid, thimerosal or combinations thereof.

2. Pharmaceutical Ingredients

Pharmaceutical active agents are also contemplated as being useful with the compositions of the present invention. Non-limiting examples of pharmaceutical active agents include anti-acne agents, agents used to treat rosacea, analgesics, anesthetics, anorectals, antihistamines, anti-inflammatory agents including non-steroidal anti-inflammatory drugs, antibiotics, antifungals, antivirals, antimicrobials, anti-cancer actives, scabicides, pediculicides, antineoplastics, antiperspirants, antipruritics, antipsoriatic agents, antiseborrheic agents, biologically active proteins and peptides, burn treatment agents, cauterizing agents, depigmenting agents, depilatories, diaper rash treatment agents, enzymes, hair growth stimulants, hair growth retardants including DFMO and its salts and analogs, hemostatics, kerotolytics, canker sore treatment agents, cold sore treatment agents, dental and periodontal treatment agents, photosensitizing actives, skin protectant/barrier agents, steroids including hormones and corticosteroids, sunburn treatment agents, sunscreens, transdermal actives, nasal actives, vaginal actives, wart treatment agents, wound treatment agents, wound healing agents, etc.

C. Kits

Kits are also contemplated as being used in certain aspects of the present invention. For instance, compositions of the present invention can be included in a kit. A kit can include a container. Containers can include a bottle, a metal tube, a laminate tube, a plastic tube, a dispenser, a pressurized container, a barrier container, a package, a compartment, a lipstick container, a compact container, cosmetic pans that can hold cosmetic compositions, or other types of containers such as injection or blow-molded plastic containers into which the dispersions or compositions or desired bottles, dispensers, or packages are retained. The kit and/or container can include indicia on its surface. The indicia, for example, can be a word, a phrase, an abbreviation, a picture, or a symbol.

The containers can dispense a pre-determined amount of the composition. In other embodiments, the container can be squeezed (e.g., metal, laminate, or plastic tube) to dispense a desired amount of the composition. The composition can be dispensed as a spray, an aerosol, a liquid, a fluid, or a semi-solid. The containers can have spray, pump, or squeeze mechanisms. A kit can also include instructions for employing the kit components as well the use of any other compositions included in the container. Instructions can include an explanation of how to apply, use, and maintain the compositions.

EXAMPLES

The following examples are included to demonstrate certain non-limiting aspects of the invention. It should be appreciated by those of skill in the art that the techniques disclosed in the examples which follow represent techniques discovered by the inventor to function well in the practice of the invention. However, those of skill in the art should, in light of the present disclosure, appreciate that many changes can be made in the specific embodiments which are disclosed and still obtain a like or similar result without departing from the spirit and scope of the invention.

Example 1

Lipstick Formulations

The Table 1 composition is a non-limiting guideline of an anhydrous lipstick having skin/lip actives and an anhydrous base. As shown in Example 3, these combinations of actives provides for a lipstick that can moisturize and lips, increase volume of lips, and reduce the appearance of lines in the lips.

TABLE 1*

| Ingredient | Amount (% w/w) |
| --- | --- |
| Sunflower Seed Oil | 10-15 |
| Jojoba Esters | 10-15 |
| Mango Butter | 3-7 |
| Volulip ™ | 1-3 |
| Tocopherol | 0.1-2% |
| Anhydrous Base | q.s. |
| TOTAL | 100 |

The Table 2 composition is a non-limiting guideline of an anhydrous lipstick of the present invention that has the actives noted in the Table 1 formulation. As shown in example 3, the anhydrous base has a pleasant tactile property.

TABLE 2*

| Phase** | Ingredient | Amount (% w/w) |
| --- | --- | --- |
| A | Oil | 20-30 |
|   | Jojoba Esters | 10-20 |
|   | *Limnanthes alba* Seed Oil/Shea Butter | 3-7 |
|   | Ethyl Macadamiate | 5-10 |
|   | Sucrose Acetate Isobutyrate | 1-5 |
| B | Sunflower Seed Wax | 1-5 |
|   | Additional Wax | 5-15 |
|   | Glyceryl Behenate/Eicosadioate | 0.1 to 2 |
| C | Mango Butter | 3-7 |
| D | Titanium Dioxide | 5-10 |
|   | Pigments/Colorants | 10-20 |
| E | Mica Silk | 2-5 |

TABLE 2*-continued

| Phase** | Ingredient | Amount (% w/w) |
|---|---|---|
| F | Volulip ™ | 0.1-2 |
|   | Tocopherol | 0.01-2 |
|   | Flavoring Agent | 0.01-2 |
|   | TOTAL | 100 |

*As indicated in the amount % column of Table 1, the amount of the ingredients can vary.
**Composition can be prepared by mixing the phase A ingredients under heat (95-100° C.). Add phase B ingredients and continue mixing under heat until mixture is homogenous. Add phase C ingredients. Cool mixture to 75-80° C. Add phase D ingredients and continue mixing. Add phase E ingredient under continued mixing. Add phase F ingredients and cool to 63-67 C. and stop mixing. Let mixture cool to room temperature(20-25° C.).

The Table 3 composition is a particular anhydrous lipstick of the present invention.

TABLE 3*

| Phase** | Ingredient | Amount (% w/w) |
|---|---|---|
| A | Castor Oil | 13.2 |
|   | Sunflower Oil | 11.9 |
|   | Jojoba Esters | 13.0 |
|   | Orange Peel Wax | 1.9 |
|   | *Limnanthes alba* Seed Oil/Shea Butter | 5.1 |
|   | Ethyl Macadamiate | 6.0 |
|   | Sucrose Acetate Isobutyrate | 2.5 |
| B | Sunflower Seed Wax | 3.34 |
|   | DR Candelilla Wax | 5.5 |
|   | Organic Beeswax | 3.4 |
|   | Glyceryl Behenate/Eicosadioate | 0.5 |
| C | Mango Butter | 5.0 |
| D | Pigments/Colorants/Titanium Dioxide*** | q.s. |
|   | Castor Oil | 2.0 |
| E | Mica Silk | 3.5 |
| F | Volulip ™ | 1.1 |
|   | Tocopherol | 0.25 |
|   | Vanilla | 0.3 |
|   | TOTAL | 100 |

*As indicated in the amount % column of Table 1, the amount of the ingredients can vary.
**Composition can be prepared by mixing the phase A ingredients under heat (95-100° C.). Add phase B ingredients and continue mixing under heat until mixture is homogenous. Add phase C ingredients. Cool mixture to 75-80° C. Add phase D ingredients and continue mixing. Add phase E ingredient under continued mixing. Add phase F ingredients and cool to 63-67 C. and stop mixing. Let mixture cool to room temperature (20-25° C.).
***Colorants are used to create a desired shade or color of the lipstick.

Example 2

Stability Data

The Table 3 composition was confirmed to be stable under a heat stability test and had a viscosity sufficient enough to mold it into a lipstick stick to be placed into a lipstick tube. The Table 3 composition had a drop point 54.1° C. and a melt point 50.0° C.

Example 3

Efficacy Data

The Table 3 formulation was used daily by 181 women over a one-week period of time. After the one-week period, 75% of the women stated that their lips felt moisturized all day long. Further, 92% of the women indicated that the formulation felt soothing, moisturizing, and comforting on lips, thereby confirming the pleasant tactile properties of the formulation. 76% of the women indicated that their lips appeared younger, voluptuous, and line-free. 85% of the women stated that the formulation replenished and conditioned their lips, leaving them looking healthy. 87% of the women stated that their lips looked smoother and felt supple. Additional in vitro tests were also performed on the Volulip™ ingredient, in which it was observed that Volulip™ stimulates collagen (+55%) and hyaluronic acid (+63%) production in human fibroblasts.

Example 4

Prophetic Examples

Additional efficacy data points of compositions of the present inventions can be determined by methods known to those of ordinary skill in the art. The following are non-limiting procedures that can be used in the context of the present invention. It should be recognized that other testing procedures can be used, including, for example, objective and subjective procedures.

Skin moisture/hydration can be measured by using impedance measurements with the Nova Dermal Phase Meter. The impedance meter measures changes in skin moisture content. The outer layer of the skin has distinct electrical properties. When skin is dry it conducts electricity very poorly. As it becomes more hydrated increasing conductivity results. Consequently, changes in skin impedance (related to conductivity) can be used to assess changes in skin hydration. The unit can be calibrated according to instrument instructions for each testing day. A notation of temperature and relative humidity can also be made. Subjects can be evaluated as follows: prior to measurement they can equilibrate in a room with defined humidity (e.g., 30-50%) and temperature (e.g., 68-72 C). Three separate impedance readings can be taken on each side of the face, recorded, and averaged. The T5 setting can be used on the impedance meter which averages the impedance values of every five seconds application to the face. Changes can be reported with statistical variance and significance.

Skin clarity and the reduction in freckles and age spots can be evaluated using a Minolta Chromometer. Changes in skin color can be assessed to determine irritation potential due to product treatment using the a* values of the Minolta Chroma Meter. The a* value measures changes in skin color in the red region. This is used to determine whether a composition is inducing irritation. The measurements can be made on each side of the face and averaged, as left and right facial values. Skin clarity can also be measured using the Minolta Meter. The measurement is a combination of the a*, b, and L values of the Minolta Meter and is related to skin brightness, and correlates well with skin smoothness and hydration. Skin reading is taken as above. In one non-limiting aspect, skin clarity can be described as L/C where C is chroma and is defined as $(a^2+b^2)^{1/2}$.

Skin dryness, surface fine lines, skin smoothness, and skin tone can be evaluated with clinical grading techniques. For example, clinical grading of skin dryness can be determined by a five point standard Kligman Scale: (0) skin is soft and moist; (1) skin appears normal with no visible dryness; (2) skin feels slightly dry to the touch with no visible flaking; (3) skin feels dry, tough, and has a whitish appearance with some scaling; and (4) skin feels very dry, rough, and has a whitish appearance with scaling. Evaluations can be made independently by two clinicians and averaged.

Clinical grading of skin tone can be performed via a ten point analog numerical scale: (10) even skin of uniform, pinkish brown color. No dark, erythremic, or scaly patches upon examination with a hand held magnifying lens. Micro-texture of the skin very uniform upon touch; (7) even skin tone observed without magnification. No scaly areas, but slight discolorations either due to pigmentation or erythema. No discolorations more than 1 cm in diameter; (4) both skin discoloration and uneven texture easily noticeable. Slight scaliness. Skin rough to the touch in some areas; and (1) uneven skin coloration and texture. Numerous areas of scaliness and discoloration, either hypopigmented, erythremic or dark spots. Large areas of uneven color more than 1 cm in diameter. Evaluations were made independently by two clinicians and averaged.

Clinical grading of skin smoothness can be analyzed via a ten point analog numerical scale: (10) smooth, skin is moist and glistening, no resistance upon dragging finger across surface; (7) somewhat smooth, slight resistance; (4) rough, visibly altered, friction upon rubbing; and (1) rough, flaky, uneven surface. Evaluations were made independently by two clinicians and averaged.

Skin smoothness and wrinkle reduction can also be assessed visually by using the methods disclosed in Packman et al. (1978). For example, at each subject visit, the depth, shallowness and the total number of superficial facial lines (SFLs) of each subject can be carefully scored and recorded. A numerical score was obtained by multiplying a number factor times a depth/width/length factor. Scores are obtained for the eye area and mouth area (left and right sides) and added together as the total wrinkle score.

Skin firmness can be measured using a Hargens ballistometer, a device that evaluates the elasticity and firmness of the skin by dropping a small body onto the skin and recording its first two rebound peaks. The ballistometry is a small lightweight probe with a relatively blunt tip (4 square mm-contact area) was used. The probe penetrates slightly into the skin and results in measurements that are dependent upon the properties of the outer layers of the skin, including the stratum corneum and outer epidermis and some of the dermal layers.

Skin softness/suppleness can be evaluated using the Gas Bearing Electrodynamometer, an instrument that measures the stress/strain properties of the skin. The viscoelastic properties of skin correlate with skin moisturization. Measurements can be obtained on the predetermined site on the cheek area by attaching the probe to the skin surface with double-stick tape. A force of approximately 3.5 gm can be applied parallel to the skin surface and the skin displacement is accurately measured. Skin suppleness can then be calculated and is expressed as DSR (Dynamic Spring Rate in gm/mm).

The appearance of lines and wrinkles on the skin can be evaluated using replicas, which is the impression of the skin's surface. Silicone rubber like material can be used. The replica can be analyzed by image analysis. Changes in the visibility of lines and wrinkles can be objectively quantified via the taking of silicon replicas form the subjects' face and analyzing the replicas image using a computer image analysis system. Replicas can be taken from the eye area and the neck area, and photographed with a digital camera using a low angle incidence lighting. The digital images can be analyzed with an image processing program and the replicas covered by wrinkles or fine lines was determined.

The surface contour of the skin can be measured by using the profilometer/Stylus method. This includes either shining a light or dragging a stylus across the replica surface. The vertical displacement of the stylus can be fed into a computer via a distance transducer, and after scanning a fixed length of replica a cross-sectional analysis of skin profile can be generated as a two-dimensional curve. This scan can be repeated any number of times along a fix axis to generate a simulated 3-D picture of the skin. Ten random sections of the replicas using the stylus technique can be obtained and combined to generate average values. The values of interest include Ra which is the arithmetic mean of all roughness (height) values computed by integrating the profile height relative to the mean profile height. Rt which is the maximum vertical distance between the highest peak and lowest trough, and Rz which is the mean peak amplitude minus the mean peak height. Values are given as a calibrated value in mm. Equipment should be standardized prior to each use by scanning metal standards of know values. Ra Value can be computed by the following equation: $R_a$=Standardize roughness; $l_m$=the traverse (scan) length; and y=the absolute value of the location of the profile relative to the mean profile height (x-axis).

In other non-limiting aspects, the efficacy of the compositions of the present invention can be evaluated by using a skin analog, such as, for example, MELANODERM™. Melanocytes, one of the cells in the skin analog, stain positively when exposed to L-dihydroxyphenyl alanine (L-DOPA), a precursor of melanin. The skin analog, MELANODERM™, can be treated with a variety of bases containing the compositions and whitening agents of the present invention or with the base alone as a control. Alternatively, an untreated sample of the skin analog can be used as a control. This test can also be used to confirm the skin exfoliation abilities of the composition (e.g., stain skin and then treat stained skin with composition to determine amount of stain removed over a targeted time period).

Skin clarity and the reduction in freckles and age spots can be evaluated using a Minolta Chromometer. Changes in skin color can be assessed to determine irritation potential due to product treatment using the a* values of the Minolta Chroma Meter. The a* value measures changes in skin color in the red region. This is used to determine whether the product is inducing irritation. The measurements were made on each side of the face and averaged, as left and right facial values. Skin clarity can also be measured using the Minolta Meter. The measurement is a combination of the a*, b, and L values of the Minolta Meter and is related to skin brightness, and correlates well with skin smoothness and hydration. Skin reading is taken as above. Skin clarity is defined as L/C where C is chroma and is defined as $(a^2+b^2)^{1/2}$.

All of the compositions and/or methods disclosed and claimed in this specification can be made and executed without undue experimentation in light of the present disclosure. While the compositions and methods of this invention have been described in terms of particular embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

The invention claimed is:

1. A lipstick comprising a combination of active ingredients comprising *Portulaca pilosa* extract, sunflower oil, jojoba esters, mango butter, and tocopherol, wherein the lipstick has a drop point of 53 to 55° C. and a melt point of 49 to 51° C.

2. A lipstick comprising *Portulaca pilosa* extract, sunflower oil, jojoba esters, mango butter, tocopherol, orange peel wax, *Limnanthes alba* seed oil, *Butyrospermum parkii*, ethyl macadamiate, sucrose acetate isobutyrate, sunflower wax, candelilla wax, beeswax, titanium dioxide, mica silk, and castor oil.

3. The lipstick of claim 1, further comprising a colorant or dye.

4. A lipstick comprising *Portulaca pilosa* extract, 10 to 15% by weight of the lipstick of sunflower oil, 10 to 15% by weight of the lipstick of jojoba esters, 3 to 7% by weight of the lipstick of mango butter, and 0.1 to 1% by weight of the lipstick of tocopherol.

5. The lipstick of claim 4, comprising 1 to 3% by weight of the lipstick of orange peel wax, 3 to 7% by weight of the lipstick of a mixture of *Limnanthes alba* seed oil and *Butyrospermum parkii*, 3 to 7% by weight of the lipstick of ethyl macadamiate, 2 to 5% by weight of the lipstick of sucrose acetate isobutyrate, 2 to 5% by weight of the lipstick of sunflower wax, 3 to 7% by weight of the lipstick of candelilla wax, 2 to 5% by weight of the lipstick of beeswax, 5 to 10% by weight of the lipstick of titanium dioxide, 2 to 5% by weight of the lipstick of mica silk, and 13 to 17% by weight of the lipstick of castor oil.

6. The lipstick of claim 1, wherein the lipstick is anhydrous.

7. A lipstick comprising *Portulaca pilosa* extract, sunflower oil, jojoba esters, mango butter, and tocopherol, wherein the lipstick does not include a fatty acid, a polyamide, and a polyglyceryl-10 behenate/eicosanedioate.

8. The lipstick of claim 1, wherein the lipstick is formed into an elongated shape and is comprised in a lipstick container, wherein the container has a base and cap.

9. A method of applying the lipstick of claim 1 to lips, the method comprising applying the lipstick to lips.

* * * * *